US00PP22480P2

(12) United States Plant Patent
Stemkens

(10) Patent No.: US PP22,480 P2
(45) Date of Patent: Jan. 31, 2012

(54) *CUPHEA* PLANT NAMED 'CUNAPIBI'

(50) Latin Name: *Cuphea ramosissima*
Varietal Denomination: Cunapibi

(75) Inventor: Henricus Godefridus Wilhelmus Stemkens, Enkhuizen (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/927,448

(22) Filed: Nov. 15, 2010

(51) Int. Cl.
*A01H 5/00* (2006.01)

(52) U.S. Cl. ..... Plt./420

(58) Field of Classification Search ..... Plt./420
See application file for complete search history.

*Primary Examiner* — Annette Para
(74) *Attorney, Agent, or Firm* — S. Matthew Edwards

(57) ABSTRACT

A new *Cuphea* plant named 'Cunapibi' particularly distinguished by the very small, light purple and red-purple bi-colored flowers, medium green foliage, vigorous, compact but decumbent and well-branched and very floriferous plant habit.

1 Drawing Sheet

Latin name of the genus and species of the plant claimed: *Cuphea ramosissima.*

Varietal denomination: 'Cunapibi'.

BACKGROUND OF THE NEW PLANT

The present invention comprises a new *Cuphea*, botanically known as *Cuphea ramosissima*, and hereinafter referred to by the variety name 'Cunapibi'.

'Cunapibi' is a product of a planned breeding program. The new cultivar 'Cunapibi' has very small, light purple and red-purple bi-colored flowers, medium green foliage, vigorous, compact but decumbent and well-branched and very floriferous plant habit.

'Cunapibi' is a F5 generation and originates from a self-ing hybridization made in a controlled breeding program in Enkhuizen, Netherlands. The female parent was an unpatented, seedling from F4 seed received from a seed bank in Ohio, USA, identified as 'E0081-2' with red-purple bicolored flowers and larger, lighter green foliage, and is less floriferous.

The pollination was made in August 2005. The resultant seed was sown in March 2006.

'Cunapibi' was selected as one flowering plant within the progeny of the stated cross in a controlled environment in May 2006 in Enkhuizen, Netherlands.

The first act of asexual reproduction of 'Cunapibi' was accomplished when vegetative cuttings were taken from the initial selection in May 2006 in a controlled environment in Enkhuizen, Netherlands.

BRIEF SUMMARY OF INVENTION

Horticultural examination of plants grown from cuttings of the plant initiated in May 2006 in Enkhuizen, Netherlands, and continuing thereafter, has demonstrated that the combination of characteristics as herein disclosed for 'Cunapibi' are firmly fixed and are retained through successive generations of asexual reproduction.

'Cunapibi' has not been observed under all possible environmental conditions. The phenotype may vary significantly with variations in environment such as temperature, light intensity and day length.

A Plant Breeder's Right for this cultivar has been applied for in CPVO on Nov. 24, 2009 (No. 2009/2471). 'Cunapibi' has not been made publicly available more than one year prior to the filing of this application.

The following traits have been repeatedly observed and are determined to be basic characteristics of the new variety. The combination of these characteristics distinguishes this *Cuphea* as a new and distinct variety.

BRIEF DESCRIPTION OF THE PHOTOGRAPH

The accompanying photographic drawing shows typical flower and foliage characteristics of 'Cunapibi' with colors being as true as possible with an illustration of this type. The photographic drawing shows a flowering potted plant of the new variety, and a close-up of the flowers.

DETAILED BOTANICAL DESCRIPTION

The plant descriptions, measurements and aforementioned photographs were taken in late August 2010 on plants that were growing in 1 gallon pots in a greenhouse in Gilroy, Calif. These plants were approximately 2 months of age.

Color Chart used: Royal Horticultural Society Colour Chart (R.H.S.) 2001

TABLE I

DIFFERENCES BETWEEN THE NEW VARIETY 'CUNAPIBI' AND A SIMILAR VARIETY: 'E0081-2' (Unpatented)

| | 'Cunapibi' | 'E0081-2' |
|---|---|---|
| Foliage size: | Smaller | Larger |
| Foliage color: | Darker green | Lighter green |
| Floriferousness: | More | Less |

Plant:

*Form, growth and habit.*—Vigorous, compact but decumbent and well-branched plant habit and is very floriferous.

*Plant height.*—20-24 cm.

*Plant height* (*inflorescence included*).—22-25 cm.

*Plant width.*—About 50-60 cm.

Roots:

*Number of days to initiate roots.*—About 10-14 days at about 22 degrees C.

*Number of days to produce a rooted cutting.*—About 21-24 days at 22 degrees C.

*Type.*—Fine, fibrous, free branching.

*Color.*—RHS N155B but whiter.

Foliage:

*Arrangement.*—Simple, opposite.

*Immature, leaf color, upper surface.*—Closest to RHS 137B but a little more yellow.

*Lower surface.*—Closest to RHS 137D.

*Mature, leaf color, upper surface.*—Closest to RHS 137B.

*Lower surface.*—Closest to RHS 137D.

*Length.*—1.9-2.1 cm.

*Width.*—1.2-1.3 cm.

*Shape.*—Ovate.

*Base shape.*—Truncate.

*Apex shape.*—Acute.

*Margin.*—Entire.

*Texture, upper surface.*—Glabrous.

*Lower surface.*—Hirsute on veins.

*Venation type.*—Pinnate.

*Color of veins, upper surface.*—Indistinct.

*Color of veins, lower surface.*—Lighter than RHS 138B.

*Petioles color.*—Lighter than RHS 138B.

*Petioles length.*—0.5-0.6 cm.

*Diameter of petiole.*—0.075 cm.

*Texture.*—Slightly hirsute.

Stem:

*Color of stem.*—Between RHS 144A and RHS 144B.

*Length of stem.*—About 30 cm.

*Diameter.*—0.2-0.25 cm.

*Length of internodes.*—2.0-2.5 cm.

*Texture.*—Hirsute.

*Color of peduncle.*—Between RHS 144A and RHS 144B.

*Length of peduncle.*—15-20 cm.

*Peduncle diameter.*—0.2 cm.

*Texture.*—Hirsute with some glandular hairs.

*Pedicel color.*—Between RHS 144A and RHS 144B.

*Pedicel length.*—2-3 cm.

*Pedicel diameter.*—0.075 cm.

*Pedicel texture.*—Hirsute and glandular hairs.

Inflorescence:

*Type.*—Terminal raceme with solitary flowers arising from the leaf axils with one flower per leaf axil, sometimes appearing so close together they appear to be cluster like. Each consisting of 2 upper petals and 4 lower petals.

*Quantity of flowers per inflorescence.*—About 15-20.

*Quantity of flowers per plant.*—Approximately 500.

*Lastingness of individual blooms on the plant.*—About 6 days.

*Fragrance.*—None.

Bud (just when opening/showing color):

*Color.*—Between RHS N79A and RHS N79B.

*Length.*—0.4-0.5 cm.

*Width.*—0.1 cm.

*Shape.*—Oblong.

Immature flower:

*Hortizontal diameter.*—0.7 cm.

*Color, upper petals, upper surface.*—RHS 58A mid petal; RHS 60B basally; with RHS N74C at the apex.

*Lower surface.*—RHS 60C with RHS 77D at the apex.

*Color, lower petals, upper surface.*—RHS 77D with RHS 71C at the mid-vein.

*Lower surface.*—RHS 77D with RHS 67C at the mid-vein.

Mature flower:

*Hortizontal diameter.*—0.8-0.9 cm.

*Vertical height.*—0.6-0.7 cm.

*Color, upper petals, upper surface.*—RHS 58A mid petal; RHS 60B basally; with RHS N74C at the apex.

*Lower surface.*—RHS 60C with RHS 77D at the apex.

*Lower petals, upper surface.*—RHS 77D to RHS 76B; with RHS 71C to RHS 71D at the mid-vein.

*Lower surface.*—Lighter than RHS 77D with RHS 67C at the mid-vein.

*Upper petal length.*—0.3 cm.

*Upper petal width.*—0.15 cm.

*Lower petal length.*—0.4 cm.

*Lower petal width.*—0.2 cm.

*Petal shape* (*all*).—Oblong.

*Apex shape.*—Obtuse to rounded.

*Margin.*—Entire.

*Petal texture, upper surface.*—Papillose.

*Lower surface.*—Papillose.

*Corolla color, inside.*—RHS 59 B to RHS 59C.

*Corolla color, outside.*—RHS N77A to RHS N77B at the mid-rib and almost translucent in between.

*Corolla length.*—0.5 cm.

*Corolla width.*—0.2 cm.

*Corolla texture, inside.*—Pilose and a few glandular hairs.

*Outside.*—Pilose.

Calyx:

*Type.*—About 20 sepals almost totally fused together along their margins but for the terminal 0.35 to 0.45 cm, forming almost cup-like floating around the corolla base.

*Color of calyx, inside.*—Basically translucent white.

*Outside.*—A muted RHS 48C with RHS 59C ribs.

*Length of calyx.*—0.3 cm.

*Apex shape.*—Each sepal is acute.

*Texture, inside.*—Very hirsute.

*Outside.*—Glandular hairs long the fused ribs (margins).

Reproductive organs:

*Pistil.*—1.

*Length.*—5.0-5.1 cm.

*Style color.*—RHS N155D but whiter with a hint of RHS 58C basally.

*Style length.*—1.5 cm.

*Stigma color.*—RHS N155C.

*Number of anthers.*—12-14; all fused to upper half of corolla with 2 pollen sacs per anther.

*Length filaments.*—0.15 cm.

*Color of filaments.*—RHS N155D but whiter with RHS 63B to RHS 63C at the apex.

*Length of anthers.*—0.35-0.5 cm.

*Anther color.*—About RHS 59B to RHS 59C.

*Pollen amount.*—Moderate.

*Color of pollen.*—RHS 6B.

*Fertility/seed set.*—Not observed.

Disease/pest resistance: Disease/pest resistance has not been observed on this hybrid.

What is claimed is:

1. A new and distinct variety of *Cuphea* plant named 'Cunapibi' substantially as illustrated and described herein.

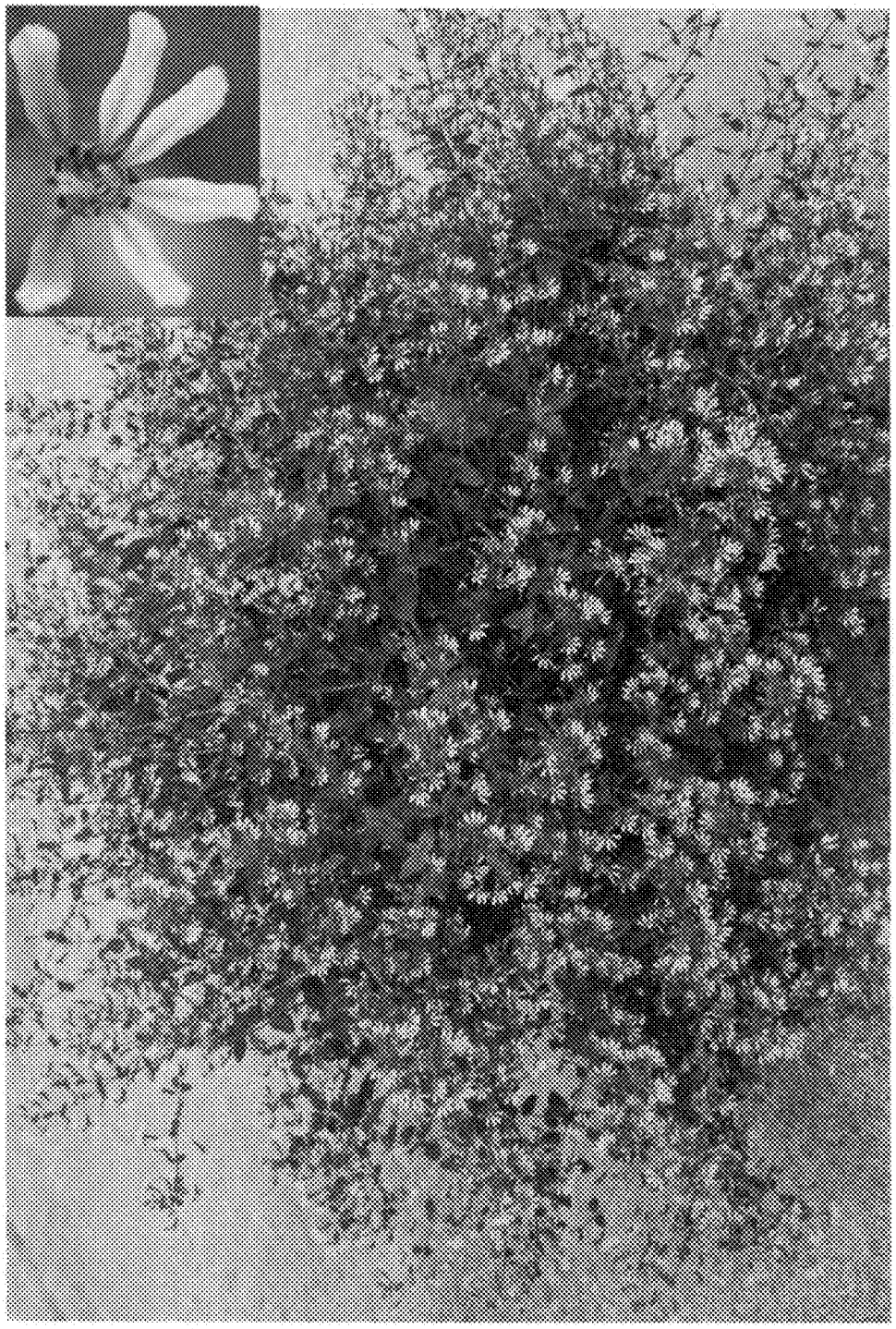

* * * * *